United States Patent [19]

Tang et al.

[11] Patent Number: 4,469,893
[45] Date of Patent: Sep. 4, 1984

[54] METHOD FOR THE PREPARATION OF NITRODIPHENYL ETHERS

[75] Inventors: David Y. Tang, Amherst; Byron R. Cotter, Grand Island, both of N.Y.; Frederick J. Goetz, Santa Ana, Calif.

[73] Assignee: Occidental Chemical Corporation, Niagara Falls, N.Y.

[21] Appl. No.: 360,533

[22] Filed: Mar. 22, 1982

[51] Int. Cl.$^3$ .................. C07C 76/02; C07C 79/35; C07C 79/36
[52] U.S. Cl. .................. 568/424; 568/585; 568/586; 260/465 F; 560/21; 562/435; 564/430
[58] Field of Search .................. 568/585, 586, 424; 260/465 F; 560/21; 562/435; 564/430

[56] References Cited

U.S. PATENT DOCUMENTS

| | | | |
|---|---|---|---|
| 3,888,932 | 6/1975 | Bayer et al. | 568/585 |
| 3,928,416 | 12/1975 | Bayer et al. | 568/585 X |
| 4,093,446 | 6/1978 | Bayer et al. | 568/585 X |
| 4,104,313 | 8/1978 | Rohe et al. | 568/585 |
| 4,259,510 | 3/1981 | Johnson | 568/585 X |

*Primary Examiner*—Bernard Helfin

*Attorney, Agent, or Firm*—James F. Tao; Arthur S. Cookfair

[57] ABSTRACT

Diphenyl esters of the formula

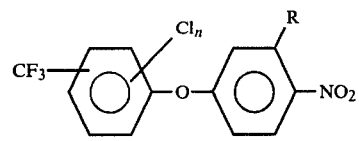

wherein R is hydrogen, carboxy, carboxylate salt or ester, formyl, cyano, alkyl, alkoxy, chloro, bromo, or N, N-dialkyl amino, are prepared by reacting a chlorofluoro-benzotrifluoride with a nitro-phenoxide of the formula

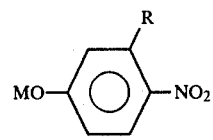

where R is defined above, and M is a cation of an alkali metal or an alkaline earth metal.

26 Claims, No Drawings

METHOD FOR THE PREPARATION OF NITRODIPHENYL ETHERS

BACKGROUND OF THE INVENTION

This invention relates to a process for preparing chloro-trifluoromethyl-nitrodiphenyl ethers having the formula

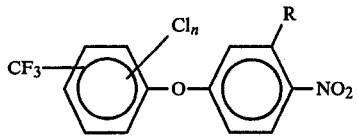

wherein n is 1 or 2 and R is hydrogen, carboxyl, carboxylate, formyl, cyano, alkyl, alkoxy, chloro, bromo, or N, N-dialkylamino. The trifluoromethylphenyl-nitrophenylethers that may be prepared by the process of this invention are members of a class of compounds useful as herbicides and/or as intermediates for the preparation of various herbicides, pesticides, dyestuffs, and pharmaceuticals. In recent years, the development of commercial utility for trifluoromethylphenyl-nitrophenylethers in the agricultural and pharmaceutical fields has led to considerable activity in the investigation of methods of preparation. The following U.S. Patents disclose the preparation and/or use of various trifluoromethylphenyl-nitrophenylethers: Nos. 4,262,152; 4,031,131; 4,259,510; 3,941,830; 3,798,276; 3,928,416; 3,784,635; 4,063,929; 4,087,272; 4,263,277; 4,263,041; 4,002,662; 4,001,005; and 3,979,437.

Various methods for the preparation of 2-chloro-4-trifluoromethyl-4¹-nitrodiphenyl ethers are known. One method, disclosed in U.S. Pat. No. 4,259,510 comprises reacting a 2-chloro-4-trifluoromethylpehnolate with a p-nitro-halobenzene. However, the phenolate reactant is not readily available commercially and, as a result, this synthesis route involves a preliminary step to prepare the phenolate. In another method, suggested in U.S. Pat. No. 4,031,131, a 3-chloro-4-halobenzotrifluoride is reacted with a phenoxide and the resultant diphenyl ether is subsequently nitrated. In addition to requiring an additional step, the subsequent nitration is inefficient and results in the production of undesired isomers. To avoid the disadvantage of a subsequent nitration step, the 3-chloro-4-halobenzotrifluoride may be reacted with a p-nitrophenoxide. However, it has been found that the presence of the nitro group drastically reduces the nucleophilicity of the phenoxide oxygen that is the reactive site, so that reaction with compounds such as 3,4-dichlorobenzotrifluoride are found to be extremely inefficient.

Nevertheless, it has now been found that, despite the adverse effect of the nitro group on the nucleophilicity of the phenoxide oxygen when the chlorohalobenzotrifluoride reactant is a chloro-fluorobenzotrifluoride such as 3-chloro-4-fluoro-benzotrifluoride, the reaction with nitrophenoxides, especially p-nitrophenoxides can be easily affected, since the reaction of the phenoxide oxygen at the fluorine site proceeds smoothly even without a catalyst to provide the trifluoromethylphenyl-nitrophenylether product in high yield. In this matter, the need for a subsequent nitration step is eliminated. Furthermore, the method of this invention, utilizing 3-chloro-4-fluorobenzotrifluoride is particularly suitable for reactions with nitrophenoxides carrying highly sensitive functional groups, such as aldehydes which might otherwise be further oxidized in a subsequent nitration step such as required by the prior art process described above.

Chloro-fluorobenzotrifluorides may be prepared by the vapor phase chloro-denitration reaction of the corresponding chloro-nitrobenzotrifluoride with a chlorinating agent. Thus, for example, 3-chloro-4-fluorobenzotrifluodie may be prepared by vapor phase chloro-denitration reaction of chlorine with 4-fluoro-3-nitrobenzotrifluoride. The chloro-denitration process is carried out under conditions of temperature and pressure appropriate for a vapor phase reaction, the exact conditions being dependent on the properties of the particular reactants employed. Typically, the process is carried out at atmospheric conditions and at a temperature in the range of about 250° to about 450° Celsius, preferably 300° to 400° C. Typical of the chloro-substituted benzotrifluorides that may be prepared by the chloro-denitration process are 2-chlorobenzotrifluoride; 3-chlorobenzotrifluoride; 4-chlorobenzotrifluoride; 3-chloro-4-fluorobenzotrifluoride; 4-chloro-3-fluorobenzotrifluoride; 2-chloro-5-fluorobenzotrifluoride; 5-chloro-2-fluorobenzotrifluoride; 2-chloro-4-fluorobenzotrifluoride; 4-chloro-2-fluorobenzotrifluoride; 3-chloro-5-fluorobenzotrifluoride; 2,5-dichloro-4-fluorobenzotrifluoride; 4,5-dichloro-2-fluorobenzotrifluoride; 3,5-dichloro-4-fluorobenzotrifluoride; and the like.

SUMMARY OF THE INVENTION

In accordance with the invention, trifluoromethylphenylnitrophenyl ethers of the formula

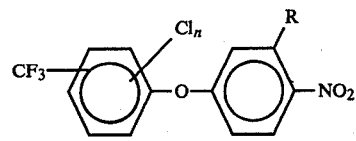

wherein n is 1 or 2 and R is hydrogen; carbaldehyde, keto; cyano; alkyl, preferably 1-6 carbon atoms; alkoxy, preferably 1-6 carbon atoms; chloro; bromo; N, N-dialkylamino, the alkyl groups being preferably 1-4 carbon atoms, carboxyl, carboxylate salts or carboxylate esters of the formula CO$_2$R' wherein R' is alkyl, preferably of 1-6 carbon atoms are prepared by reacting a chloro-fluoro-benotrifluoride of the formula

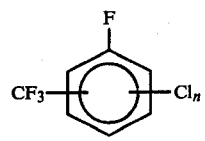

where n is defined above, with a nitro-phenoxide of the formula

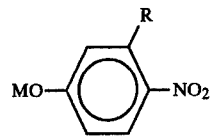

where R is defined above, and M is a cation of an alkali metal or alkaline earth metal.

Typical chloro-fluorobenzotrifluoride reactants that may be employed in the process of this invention are 2-chloro-5-fluorobenzotrifluoride; 5-chloro-2-fluorobenzotrifluoride; 2-chloro-4-fluorobenzotrifluoride; 4-chloro-2-fluorobenzotrifluoride; 3-chloro-5-fluorobenzotrifluoride; 3-chloro-4-fluorobenzotrifluoride; 4-chloro-3-fluorobenzotrifluoride; 2,5-dichloro-4-fluorobenzotrifluoride 4,5-dichloro-2-fluorobenzotrifluoride 3,5-dichloro-4-fluorobenzotrifluoride and the like.

The nitrophenoxide may be employed as shown as a previously prepared reactant or may be prepared in situ in the reaction mixture from the corresponding nitrophenol and an alkaline earth metal hydroxide or carbonate or, preferably an alkali metal hydroxide or carbonate. The preferred nitrophenoxides are the sodium or potassium salts. When a nitrophenol bearing a carboxylic group is employed as a reactant it is preferred to employ the di-salt of an alkali or alkaline earth metal.

The reaction is preferably carried out in the presence of a dipolar aprotic solvent. Suitable solvents include, for example, dimethylsulfoxide, sulfolane, N-methyl-2-pyrrolidone, N, N-dimethylformamide, and the like. The reaction may be run neat utilizing the chloro-fluorobenzotrifluoride reactant as the liquid reaction medium in the presence of a phase transfer catalyst, such as a quaternary ammonium salt, a quaternary phosphonium halide or a crown ether catalyst.

The temperature at which the reaction is carried out may vary considerably but is preferably maintained in the range of about 50° to about 300° Celsius, and most preferably, in the range of about 100° to about 200° Celsius. The process is preferably carried out at atmospheric pressure. However, autogenous pressure may be employed if desired, to allow the use of higher temperatures.

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

EXAMPLE 1

In a continuous process, about 8 parts per hour of 4-fluoro-3-nitrobenzotrifluoride vapors and about 15 parts per hour of chlorine gas were passed simultaneously through a vapor phase reactor maintained at a temperature of about 320° C. and the reaction product vapors were condensed and collected. The process was continued until about 40 parts of 4-fluoro-3-nitrobenzotrifluoride had been passed through the reactor, yielding about 36.3 parts of 3-chloro-4-fluoro benzotrifluoride product. The structure of the product was confirmed by spectral analysis.

EXAMPLE 2A

About 500 parts of aqueous nitric acid was added slowly, with stirring, to a reaction vessel containing about 400 parts of 3-chloro-4-fluorobenzotrifluoride. The temperature of the reaction mixture was maintained at about 40° C. during the addition, then raised to about 60° C. and maintained thereat for about 5 hours. The reaction mixture was allowed to settle. The aqueous layer was removed and the organic layer was washed twice with 500 parts of water, treated several times with a saturated solution of sodium bicarbonate, washed with water again, dried over anhydrous magnesium sulfate, and filtered. The filtrate was distilled at reduced pressure to yield 347 parts of 5-chloro-4-fluoro-2-nitrobenzotrifluoride.

EXAMPLE 2B

In a continuous process, about 14 parts per hour of 5-chloro-4-fluoro-2-nitrobenzotrifluoride vapors and about 12 parts per hour of chlorine gas were passed simultaneously through a vapor phase reactor maintained at a temperature of about 320° to 380° C. The vaporized reaction product was condensed and collected. The process was continued until about 14.7 parts of 5-chloro-4-fluoro-2-nitrobenzotrifluoride had been added and 14.7 parts of 2,5-dichloro-4-fluorobenzotrifluoride product was collected. The structure of the product was confirmed by gas chromatography—mass spectrum, $F^{19}$ and $C^{13}$ nuclear magnetic resonance analysis.

EXAMPLE 3

In a continuous process, about 14 parts per hour of 2-fluoro-5-nitrobenzotrifluoride vapors and about 12 parts per hour of chlorine gas were passed simultaneously through a vapor phase reactor maintained at a temperature of about 320° to 380° C. The vaporized reaction product was condensed and collected. The process was continued until about 20 parts of 2-fluoro-5-nitrobenzotrifluoride and about 17.3 parts of chlorine gas had been passed through the reactor. Analysis of the reaction product indicated 16.7 parts of 5-chloro-2-fluorobenzotrifluoride, a yield of 89%. The structure of the product was confirmed by gas chromatography—mass spectrum $F^{19}$ and $C^{13}$ nuclear magnetic resonance analysis.

EXAMPLE 4

14.1 parts of 5-fluoro-2-nitrobenzotrifluoride vapors and 12.1 parts of chlorine gas were passed simultaneously, over a one-hour period, through a vapor-phase reactor maintained at a temperature of about 320° to 380° C. The vaporized reaction product was condensed and collected. Analysis of the reaction product indicated 12.6 parts of 2-chloro-5-fluorobenzotrifluoride, a yield of 94%. The structure of the product was confirmed by gas chromatography—mass spectrum $F^{19}$ and $C^{13}$ nuclear magnetic resonance analysis.

EXAMPLE 5

A mixture of 2.66 parts of potassium 4-nitrophenoxide; 3.9 parts of 3-chloro-4-fluorobenzotrifluoride and 126 parts of sulfolane was heated to about 142° C. and maintained thereat, with stirring for about 2 hours, then cooled to about room temperature, diluted with water and extracted with diethylether. The ether layer was dried and the ether removed under reduced pressure to yield 6.2 parts of a crude product. Gas chromatographic-mass spectrum analysis confirmed the major product as 4-(2-chloro-4-trifluoromethylphenoxy)-nitrobenzene.

EXAMPLE 6

A mixture of 2 parts of potassium 4-nitrophenoxide; 2.3 parts of 3-chloro-4-fluorobenzotrifluoride and 26 parts of N-methylpyrrolidone, was sealed in a pressure vessel and heated to about 160° C. The reaction mixture was maintained at that temperature, under autogenous pressure, with vigorous stirring for about 3 hours, then cooled to about room temperature diluted with water and extracted with diethyl ether. The ether layer was dried and concentrated. Analysis of the reaction product, by gas chromatographic-mass spectrum confirmed the major product to be 4-(2-chloro-4-trifluoromethylphenoxy)-nitrobenzene.

EXAMPLE 7

The process of Example 6 is repeated except that in place of 3-chloro-4-fluorobenzotrifluoride, there is substituted an equal amount of 2-chloro-5-fluorobenzotrifluoride, and the product prepared is 4-(4-chloro-3-trifluoro-methylphenoxy)nitrobenzene.

EXAMPLE 8

The process of Example 6 is repeated except that in place of 3-chloro-4-fluorobenzotrifluoride there is substituted an equal amount of 5-chloro-2-fluorobenzotrifluoride and the product prepared is 4-(4-chloro-2-trifluoromethylphenoxy)nitrobenzene.

EXAMPLE 9

The process of Example 6 is repeated except that in place of 3-chloro-4-fluorobenzotrifluoride, there is substituted an equimolar amount of 2,5-dichloro-4-fluorobenzotrifluoride and the product prepared is 4-(2,5-dichloro-4-trifluoromethylphenoxy)nitrobenzene.

EXAMPLE 10

To a solution of 10 parts of 5-hydroxy-2-nitrobenzoic acid in 320 parts of methanol, was added 6.1 parts of potassium hydroxide. The mixture was allowed to react under ambient conditions for about one hour. The resulting dipotassium salt of 5-hydroxy-2-nitrobenzoic acid was dried by removing the solvent under reduced pressure. The di-potassium salt was then combined with 380 parts of sulfolane; 310 parts of N-methyl-2-pyrrolidone; and 50 parts of 3-chloro-4-fluorobenzotrifluoride. The mixture was heated to about 150° C. and maintained thereat for about 24 hours, then cooled, acidified with hydrochloric acid and extracted with diethyl ether. The ether extract was washed with water and dried over anhydrous magnesium sulfate. The ether and the excess 3-chloro-4-fluorobenzotrifluoride were removed under vacuum to yield a crude yellow-brown product. Mass spectrographic analysis indicated 5-(2-chloro-4-trifluoromethylphenoxy)-2-nitrobenzoic acid as a major component.

EXAMPLE 11

A mixture of 16.7 parts of 5-hydroxy-2-nitrobenzaldehyde and 6.6 parts of potassium hydroxide in about 120 parts of methanol was stirred at room temperature for about one hour. The solvent was then evaporated at reduced pressure to recover the potassium salt of the phenolates as a dry solid. To this was added 30 parts of 3-chloro-4-fluorobenzotrifluoride and about 154 parts of N-methyl-2-pyrrolidone. The mixture was stirred at 140°–150° C. for about one hour, then cooled, diluted with water, acidified with 10% hydrochloric acid, and extracted several times with diethyl ether. The ether layer was washed with a 10% aqueous potassium hydroxide solution. Then with water, and dried over anhydrous magnesium sulfate. The dried ether solution was then concentrated by evaporation under reduced pressure to yield 5-(2-chloro-4-trifluoromethylphenoxy)-2-nitrobenzaldehyde as the major product. The structure of 5-(2-chloro-4-trifluoromethylphenoxy)-2-nitrobenzaldehyde was confirmed by gas chromatography—mass spectrum analysis.

What is claimed is:

1. A process for the preparation of diphenyl ethers of the formula

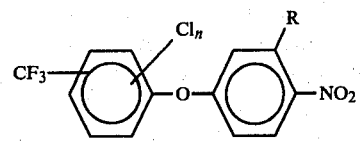

wherein n is 1 or 2, R is hydrogen; formyl; cyano; alkyl, of 1–6 carbon atoms; alkoxy, of 1–6 carbon atoms; chloro; bromo; N, N-dialkyl amino, the alkyl group being preferably 1–4 carbon atoms; carboxyl, carboxylate salts; or carboxylate esters of the formula $CO_2R'$ wherein R' is alkyl of 1–6 carbon atoms, which comprises reacting a chlorofluorobenzotrifluoride of the formula

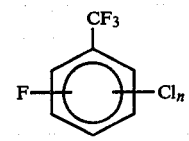

where n is defined above, with a nitro-phenoxide of the formula

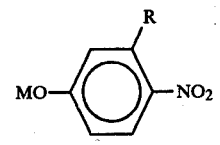

where R is defined above, and M is a cation of an alkali metal or an alkaline earth metal.

2. A process according to claim 1 wherein the chlorofluorobenzotrifluoride is 3-chloro-4-fluorobenzotrifluoride.

3. A process according to claim 1 wherein the chlorofluorobenzotrifluoride is 2-chloro-5-fluorobenzotrifluoride.

4. A process according to claim 1 wherein the chlorofluorobenzotrifluoride is 5-chloro-2-fluorobenzotrifluoride.

5. A process according to claim 1 wherein the chlorofluorobenzotrifluoride is 2,5-dichloro-4-fluorobenzotrifluoride.

6. A process according to claim 1, carried out in a dipolar aprotic solvent.

7. A process according to claim 6 wherein M is a cation of an alkali metal.

8. A process according to claim 7 wherein R is hydrogen.

9. A process according to claim 7 wherein R is an alkali metal carboxylate.

10. A process according to claim 7 wherein R is formyl.

11. A process according to claim 7 carried out at a temperature of about 50° to about 300° Celsius.

12. A process according to claim 11 carried out at autogenous pressure.

13. A process according to claim 11 carried out at atmospheric pressures.

14. A process for the preparation of 5-(2-chloro-4-trifluoromethylphenoxy)-2-nitrobenzoic acid which comprises reacting 3-chloro-4-fluorobenzotrifluoride with a di-salt of 5-hydroxy-2-nitrobenzoic acid and acidifying the product with a strong inorganic acid.

15. A process according to claim 14 wherein the di-salt is the di-potassium salt of 5-hydroxy-2-nitrobenzoic acid.

16. A process according to claim 15 carried out at about 50° to about 300° Celsius in the presence of a dipolar aprotic solvent.

17. A process for the preparation of 4-(2-chloro-4-trifluoromethyl-phenoxy)-nitrobenzene which comprises reacting 3-chloro-4-fluorobenzotrifluoride with a 4-nitrophenoxide.

18. A process according to claim 17 wherein the 4-nitrophenoxide is potassium 4-nitrophenoxide and the process is carried out at a temperature of about 50° to about 300° Celsius in the presence of a dipolar aprotic solvent.

19. A process for the preparation of 5-(2-chloro-4-trifluoromethylphenoxy)-2-nitrobenzaldehyde which comprises reacting 3-chloro-4-fluorobenzotrifluoride with 5-hydroxy-2-nitrobenzaldehyde.

20. A process according to claim 19 carried out at a temperature of about 50° to about 300° Celsius in the presence of a dipolar aprotic solvent.

21. A process for the preparation of 4-(4-chloro-3-trifluoromethylphenoxy)-nitrobenzene which comprises reacting 2-chloro-5-fluorobenzotrifluoride with a 4-nitrophenoxide.

22. A process according to claim 21 wherein the 4-nitrophenoxide is potassium 4-nitrophenoxide and the process is carried out at a temperature of about 50° to about 300° Celsius in the presence of a dipolar aprotic solvent.

23. A process for the preparation of 4-(4-chloro-2-trifluoromethylphenoxy)-nitrobenzene which comprises reacting 5-chloro-2-fluorobenzotrifluoride with a 4-nitrophenoxide.

24. A process according to claim 23 wherein the 4-nitrophenoxide is potassium 4-nitrophenoxide and the process is carried out at a temperature of about 50° to about 300° Celsius in the presence of a dipolar, aprotic solvent.

25. A process for the preparation of 4-(2,5-dichloro-4-trifluoromethylphenoxy)-nitrobenzene which comprises reacting 2,5-dichloro-4-fluorobenzotrifluoride with a 4-nitrophenoxide.

26. A process according to claim 25 wherein the 4-nitrophenoxide is potassium 4-nitrophenoxide and the process is carried out at a temperature of about 50° to about 300° Celsius in the presence of a dipolar, aprotic solvent.

* * * * *